United States Patent [19]

Slamon et al.

[11] Patent Number: 4,918,162
[45] Date of Patent: Apr. 17, 1990

[54] ASSAYS AND ANTIBODIES FOR N-MYC PROTEINS

[75] Inventors: Dennis J. Slamon, Woodland Hills; Lawrence M. Souza, Thousand Oaks, both of Calif.

[73] Assignee: The Regents of the University of California, Berkeley, Calif.

[21] Appl. No.: 253,933

[22] Filed: Oct. 5, 1988

Related U.S. Application Data

[63] Continuation-in-part of Ser. No. 860,276, May 6, 1986. Pat. 4918162, abandoned.

[51] Int. Cl.$^4$ .............................................. C07K 7/10
[52] U.S. Cl. ................................... 530/324; 530/350; 424/88
[58] Field of Search ..................... 530/350, 324; 435/172.3; 424/88

[56] References Cited

PUBLICATIONS

Stanton et al., Proc. Natl. Acad. Sci. U.S.A., vol. 83, pp. 1772–1776 (Mar. 1986).
Slamon et al., Science, vol. 232, pp. 768–772 (May 9, 1987).
Schwab et al., (1983), Nature 305:245.
Kohl et al., (1983), Cell 35:359.
Kohl et al., (1986), Nature 319:73.
Brodeur et al., (1984), Science 224:1121.
Seeger et al., (1985), New Engl. J. Med., 313:1111.
Lee et al., (1984), Nature, 309:458.
Nau et al., (1986), Proc. Natl. Acad. Sci. U.S.A., 83:1092–1096.

Primary Examiner—Margaret Moskowitz
Assistant Examiner—Christina Chan
Attorney, Agent, or Firm—Townsend & Townsend

[57] ABSTRACT

Methods and compositions are provided for identifying patients suffering from cancer, particularly neural and neuroendocrine cancers. It has been found that the protein expression product of the human N-mcy proto-oncogene may be detected in certain biological specimens, particularly tissue specimens and sputum samples. By obtaining immunogenic N-myc polypeptides, either synthetically or by isolation from a natural source, antibodies specific for the N-myc protein are obtained. Those antibodies may then be used in immunological techniques for detecting the presence of N-myc in the biological samples. In particular, the antibodies may be employed in immunohistochemical techniques to detect the N-myc protein in prepared tissue and sputum samples.

3 Claims, 3 Drawing Sheets

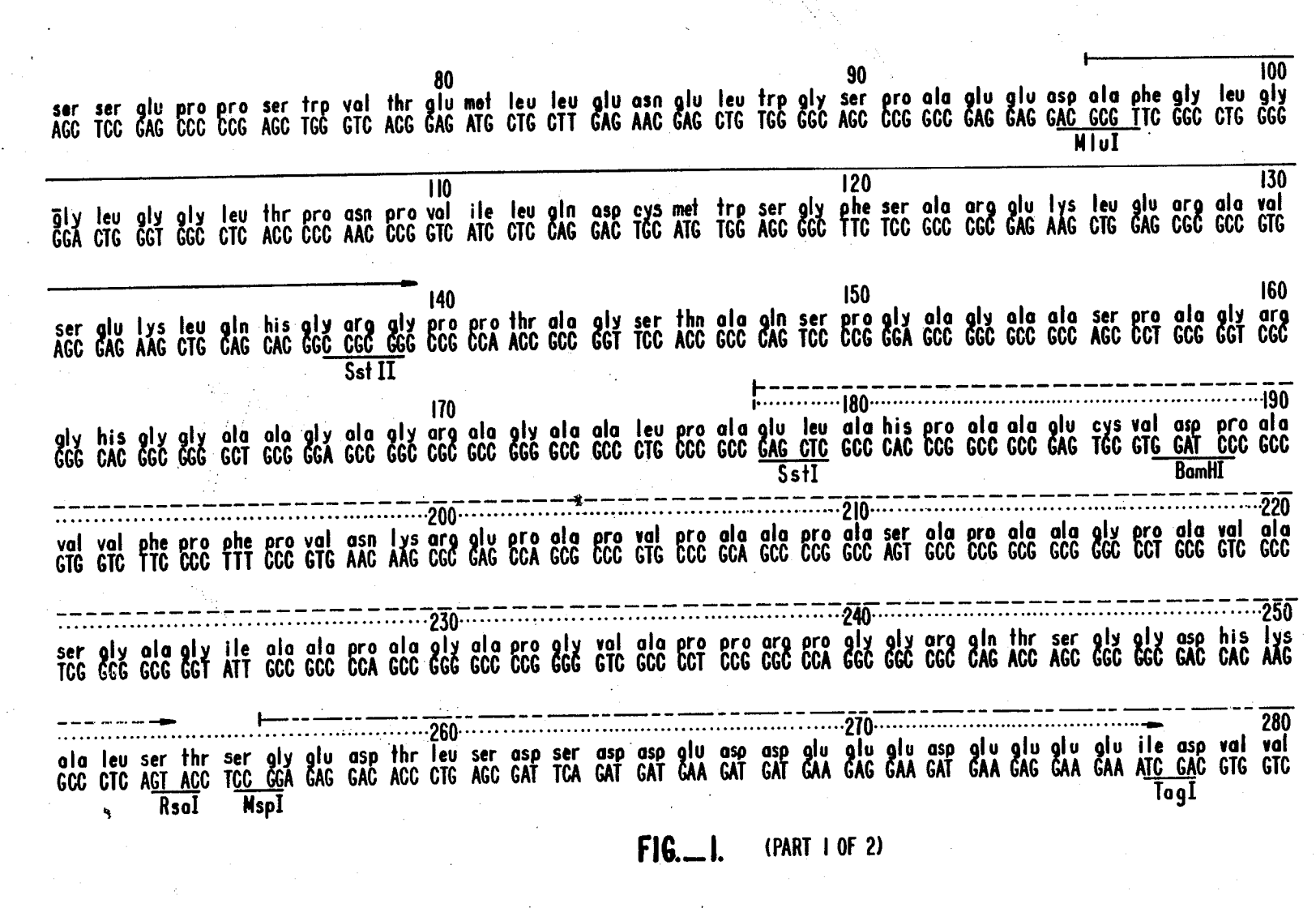

FIG._1. (PART 1 OF 2)

```
                                                                                                     310
                                                                                         thr val arg pro lys asn ala ala leu gly pro
                                                                                         ACT GTG CGT CCC AAG AAC GCA GCC CTG GGT CCC
                                                         300
                                 thr lys ala val thr thr phe thr ile
                                 ACC AAG GCT GTC ACC ACA TTC ACC ATC
                 290
  thr val glu lys arg arg ser ser asn
  ACT GTG GAG AAG CGG AGG TCC TCC AAC
                                                                                                                          340
                                                                              his gln gln his asn tyr ala ala pro ser tyr val glu
                                                                              CAC CAG CAG CAC AAC TAT GCC GCC CCC TCC TAC GTG GAG
                                 320
  gly arg ala gln ser ser glu leu leu ile leu lys arg cys leu pro
  GGG AGG GCT CAG TCC AGC GAG CTC CTG ATC CTC AAA CGA TGC CTT CCC
       MspI
                                                                                                                                            370
                                                                                                          ile pro pro lys ala lys ser leu
                                                                                                          ATC CCC CCA AAG GCT AAG AGC TTG
                                 350
  ser glu asp ala pro gln lys ile lys ser glu lys ser val
  AGT GAG GAT GCA CCC CAG AAG ATA AAG AGT GAG AAG AGT GTC
                                                                                                                          400
                                                                              arg asn his asn ile leu glu arg gln arg asn asp leu arg ser ser
                                                                              CGG AAT CAC AAC ATC CTG GAG CGG CAG CGG AAC GAC CTT CGG TCC AGC
                                 380
  ser pro arg asn ser asp ser glu ser
  AGC CCC CGA AAC TCT GAC AGT GAG TCG
                                                                                                                                            430
                                                                                                                          thr glu tyr val
                                                                                                                          ACT GAG TAT GTC
                         410
  phe leu thr leu arg asp his val pro glu leu val lys asn glu lys ala ala lys val val ile leu lys ala
  TTT CTC ACG CTC AGG GAC CAC GTG CCG GAG TTG GTA AAG AAT GAG AAG GCC GCC AAG GTG GTC ATT TTG AAA GCC
                                         MspI
                                                                                                                          460
                                                                                                          lys lys ile glu his
                                                                                                          AAG AAA ATT GAA CAC
                                 440                                      450
  his ser leu gln ala glu his gln leu leu glu lys glu lys gln ala arg gln gln gln leu his
  CAC TCC CTC CAG GCC GAG CAC CAG CTT CTG GAA AAG GAA AAG CAG GCA AGA CAG CAG CAG TTG CTA
  ala arg thr cys AM
  GCT CGG ACT TGC TAG ACGGTTCTCAAAACTGGACAGTCACTGCCACTGCCACTTTGCACATTTTGATTTTTTTTTTAAACAAACATTGTGTTGACATTAAGAATGTTGGTTTACTTTCAA
                                                                                                         HincII

FIG._1.      (PART 2 OF 2)
```

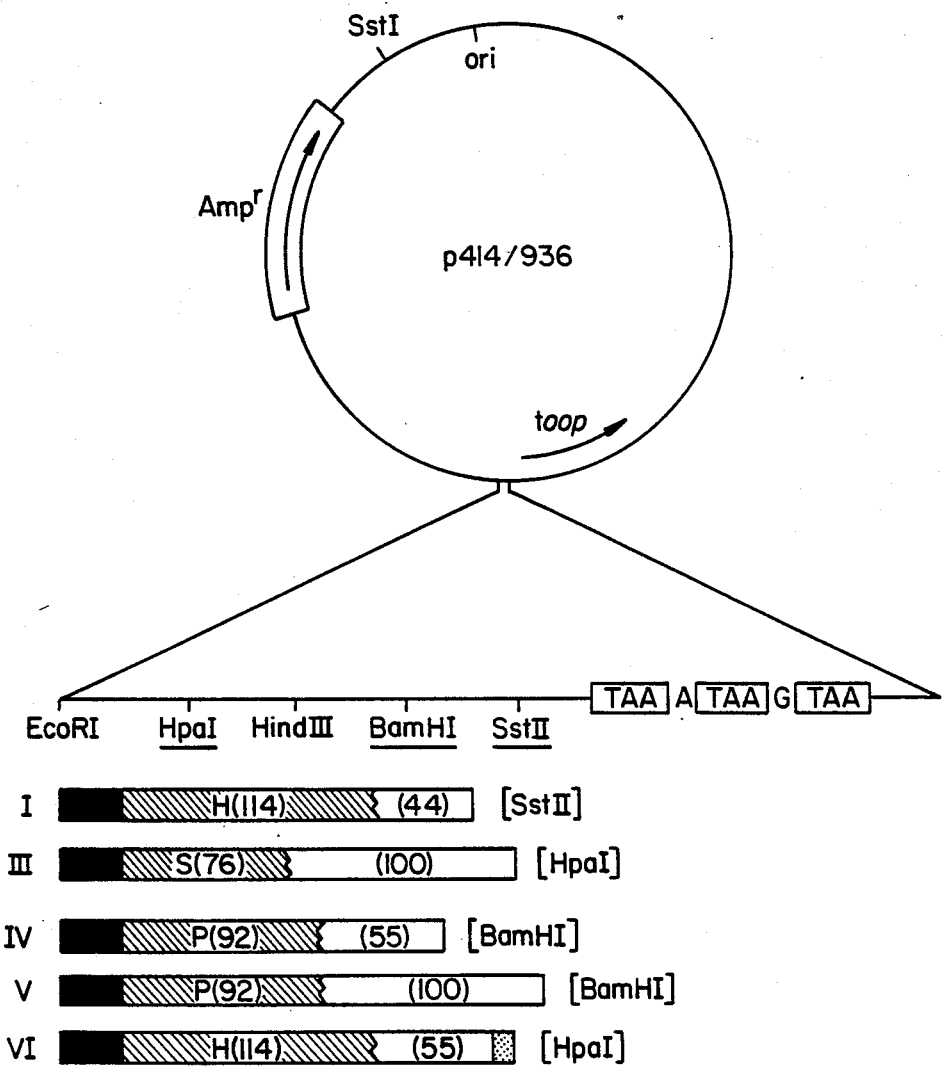
FIG._2.

ASSAYS AND ANTIBODIES FOR N-MYC PROTEINS

This is a continuation of application Ser. No. 860,276, filed May 6, 1986, now abandoned.

BACKGROUND OF THE INVENTION

1. Field of the Invention

Oncogenes are genes that, when activated or altered, may be involved in transformation of normal cells to a neoplastic phenotype. Numerous oncogenes have been identified in both humans and animals, and the transformation mechanisms associated with each vary widely. Frequently, the oncogene has a corresponding normal cellular gene referred to as a proto-oncogene, and modification of either the expression or the structure of the proto-oncogene may result in neoplatic transformation. For example, alteration of a single nucleotide in the ras proto-oncogene renders the host cell neoplastic, while transposition of the c-myc proto-oncogene results in increased expression and neoplastic transformation of the host. Another such example would be translocation of the c-abl proto-oncogene which results in a unique transcript and protein found in chronic myelogenous leukemia (CML).

N-myc is a human proto-oncogene which was originally identified because of its similarity to the viral c-myc oncogene. Gene amplification and/or increased expression of N-myc has been found in certain tumor cell lines as well as both primary and metastatic tumors. In particular, N-myc has been associated with neuroblastomas, retinoblastomas, and small-cell lung cancers (SCLC). Additionally, expression of N-myc has been found to complement mutant ras genes in tumorigenic conversion of rat fibroblasts. Thus, N-myc appears to be involved in the pathogenesis of certain human malignancies.

It would be desirable to isolate and characterize the N-myc gene product and to provide assay methods and reagent compositions useful for identifying and diagnosing tumors in which N-myc is expressed. In particular, it would be desirable to obtain antigenic reagents capable of eliciting antibodies specific for the N-myc gene product and to use such antibodies in diagnosis and treatment of N-myc related cancers.

2. Description of Pertinent References

N-myc proto-oncogenes were first identified in human neuroblastoma cell lines which showed a 25 to 700-fold amplification of the gene. Schwab et al. (1983) Nature 305:245, and Kohl et al. (1983) Cell 35:359. The sequence of the N-myc gene is reported in Kohl et al. (1986) Nature 319:73. Amplification and increased transcription of N-myc in untreated primary neuroblastomas and retinoblastomas are reported in Brodeur et al. (1984) Science 224:1121; Seeger et al. (1985) New Engl. J. Med. 313:1111; and Lee et al. (1984) Nature 309:458. Amplification and increased transcription of N-myc have also been observed in human small-cell lung cancers. Nau et al. (1986) Proc. Natl. Acad. Sci. U.S.A. 83:1092-1096.

SUMMARY OF THE INVENTION

The present invention provides methods and compositions for identifying and monitoring human cancers, particularly cancers which have neural or neuroendocrine properties such as neuroblastomas, retinoblastomas, and small-cell lung cancers. The methods rely on detection of N-myc protein in a biological specimen, usually a cell sample such as a tissue sample or sputum sample. Presence of the N-myc protein in the biological specimen may be diagnostic and/or prognostic of the cancer.

Polypeptides and antibodies thereto are utilized for detecting the N-myc proteins, where the polypeptides are associated with immunogenic sites on the protein. The polypeptides may be natural or synthetic and will include at least six contiguous amino acids of the natural protein, usually including at least 9 contiguous amino acids, more usually including at least 12 contiguous amino acids, representing detectable epitope(s) on the N-myc protein. Such polypeptides include the N-myc protein in substantially pure form as well as fragments thereof. Monoclonal or polyclonal antibodies against the polypeptides are prepared by conventional techniques, and the antibodies and polypeptides are utilized in a variety of conventional immunologic assay and histochemical staining techniques for detection of N-myc protein in the biological specimen.

The present invention is particularly useful for distinguishing among morphologically similar tumor types. For example, it is frequently difficult to distinguish various round cell tumors of childhood, such as neuroblastomas, neuroepitheliomas, Ewing sarcomas, rahbdomyosarcomas, and lymphomas. Since the treatment required depends greatly on the nature of the tumor, it is important to be able to distinguish the tumor type at an early stage. Use of the present invention will allow early identification of neuroblastomas and other tumors expressing N-myc. The present invention will also be useful for identifying the cellular origin of micrometastases in non-primary sites such as lymph nodes and bone marrow, and the amount of the N-myc protein expressed, measured by the intensity of staining, may correlate with the disease prognosis. The present invention also promises to provide early detection of small cell lung cancers, particularly by detection of cancer cells in sputum and/or lung lavage samples.

In a particular aspect of the present invention, novel DNA molecules are provided for expressing the N-myc polypeptides. The DNA molecules include at least a portion of the N-myc gene under the transcriptional control of a heterologous promoter, and usually also include an origin of replication. The N-myc gene may be natural or synthetic, and the DNA molecule expressed in vitro to produce the N-myc polypeptides.

BRIEF DESCRIPTION OF THE DRAWINGS

FIG. 1 represents the nucleotide sequence together with the deduced amino acid sequence for the N-myc 1 clone described in the Experimental section hereinafter.

FIG. 2 illustrates the P414/936 plasmid used in expressing various N-myc 1 fragments, as described in detail in the Experimental section hereinafter.

DESCRIPTION OF THE SPECIFIC EMBODIMENTS

According to the present invention, methods for identifying cancers in human patients rely on detection of the expression product of the human N-myc proto-oncogene in a biological specimen, typically body fluids, tissue, or sputum samples. Conveniently, detection is accomplished by immunological techniques, such as immunohistochemical staining of a cell sample employing either monoclonal or polyclonal antibodies specific for the N-myc protein. Detection of the N-myc protein is particularly useful in distinguishing specific cancers, such as neuroblastomas, from morphologically similar cancers and for the early detection and differential diagnosis of cancers, such as small-cell lung cancers.

N-myc is a human proto-oncogene which has been associated with the pathogenesis of a number of human tumors, particularly neural and neuroendocrine associated tumors such as neuroblastomas, retinoblastomas, and small-cell lung cancers. As demonstrated by the work reported herein, the expression product of the N-myc gene is a doublet phosphoprotein including polypeptides having a molecular weight below about 65 kD, usually being in the range from about 60 to 65 kD, more specifically being of about 62 kD and 64 kD, respectively, where it is believed that the 62 kD species represents the gene product prior to phosphorylation. These molecular weights, of course, are only approximate and subject to experimental error in the measurement techniques reported in the Experimental section hereinafter. The protein has a half-life of about 30 to 50 minutes, and is located within the cell nucleus where 40 to 50% is associated with the nuclear matrix. As further demonstrated herein, neoplastic transformation of certain neural and neuroendocrine associated cells is characterized by detectable expression of the N-myc protein.

The polypeptides of the present invention will be either haptenic or antigenic, including at least 6 amino acids, usually at least 9 amino acids, and more usually 12 or more amino acids found contiguously within the natural N-myc protein. The contiguous amino acids may be located within any region of either of the doublet polypeptides and will correspond to at least one epitopic site which is characteristic of the protein. By characteristic, it is meant that the epitopic site will allow immunologic detection of the N-myc protein in a cell sample with reasonable assurance, in most cases allowing N-myc to be immunologically distinguished from other related proteins, such as c-myc. In other cases, however, the epitopic site(s) will be cross-reactive with other proteins, such as c-myc.

As reported in greater detail in the Experimental section hereinafter, six particular polypeptides within the carboxyl terminal 394 amino acids of the putative N-myc protein (as reported by Kohl et al. (1986), supra.) have been identified which are capable of eliciting antibodies useful in the present invention. The sequences of these polypeptides (using the standard single letter designation) are as follows:

| (I) | AFGLGGLGGL LERAVSEKLQ | TPNPVILQDC HGRG; | MWSGFSAREK |
|---|---|---|---|
| (II) | ELAHPAAECV APASAPAAGP RPGGRQTSGG | DPAVVFPFPV AVASGAGIAA DHKALS; | NKREPAPVPA PAGAPGVAPP |
| (III) | ELAHPAAECV APASAPAAGP RPGGRQTSGG DEEEDEEEEI; | DPAVVFPFPV AVASGAGIAA DHKALSTSGE | NKREPAPVPA PAGAPGVAPP DTLSDSDDED |
| (IV) | GEDTLSDSDD RSSSNTKAVT | EDDEEEDEEE TFTITVRPKN | EIDVVTVEKR AALGP; |
| (V) | GRAQSSELIL SEDAPPQKKI SPRNSDSEDS FLTLRDHVP; | KRCLPIHQQH KSEASPRPLK ERRRNHNILE and | NYAAPSPYVE SVIPPKAKSL RQRRNDLRSS |
| (VI) | ELVKNEKAAK LLLEKEKLQA | VVILKKATEY RQQQLLKKIE | VHSLQAEEHQ HARTC. |

Of these six polypeptides, it has been found that II and III are capable of eliciting antibodies having very high specificity and affinity for the N-myc protein and which are free from reactivity with c-myc and other proteins. In contrast, antibodies raised against polypeptide V appear to cross-react with c-myc protein. While antibodies raised against all six polypeptides react with N-myc in immunoprecipitation assays with lysates of neuroblastoma cell lines, only II, III, and V elicit antibodies which histochemically stain the whole cells under the conditions tested.

The N-myc polypeptides may be natural, i.e., the entire N-myc protein or fragments thereof isolated from a natural source, or may be synthetic. The natural polypeptides may be isolated from natural sources, such as neuroblastoma and retinoblastoma cell lines known to produce the N-myc protein, by conventional techniques such as affinity chromatography. Conveniently, polyclonal or monoclonal antibodies obtained according to the present invention may be used to prepare a suitable affinity column by well known techniques. Such techniques are taught, for example, in Hudson and Hay, *Practical Immunology*, Blackwell Scientific Publications, Oxford, United Kingdom, 1980, Chapter 8.

Synthetic polypeptides which are immunologically cross-reactive with the natural N-myc protein may be produced by either of two general approaches. First, polypeptides having fewer than about 50 amino acids, more usually fewer than about 20 amino acids, may be synthesized by the well-known Merrifield solid-phase synthesis method where amino acids are sequentially added to a growing chain (Merrifield (1963) J. Am. Chem. Soc. 85:2149–2156). The amino acid sequences of such synthetic polypeptides may be based on the sequence of FIG. 1 described in the Experimental section hereinafter, or on the sequence for the entire N-myc gene reported in Kohl et al. (1986), supra.

The second and preferred method for synthesizing the polypeptides of the present invention involves the expression in cultured cells of recombinant DNA molecules encoding a desired portion of the N-myc gene. The N-myc gene may itself be natural or synthetic with the natural gene obtainable from cDNA or genomic libraries using available probes, such as pNb-1 (Schwab et al. (1983) Nature 305:245). Alternatively, probes may be synthesized based on the DNA sequences reported in FIG. 1, as described in the Experimental section hereinafter. Suitable cDNA and genomic libraries may be obtained from human cell lines known to contain the N-myc gene, such as the LA-N-5 and IMR-32 human neuroblastoma cell lines. Alternatively, polynucleotides may be synthesized by well-known techniques. For example, short single-stranded DNA fragments may be prepared by the phosphoramidite method described by Beaucage and Carruthers (1981) Tett. Letters 22:1859–1862. A double-stranded fragment may then be obtained either by synthesizing the complementary strand and annealing the strands together under appropriate conditions or by adding the complementary strand using DNA polymerase with an appropriate primer sequence. Particular DNA sequences may be based on FIG. 1 herein, or on the sequence reported by Kohl et al. (1986), supra.

The natural or synthetic DNA fragments coding for a desired N-myc fragment will be incorporated in DNA constructs capable of introduction to and expression in an in vitro cell culture. Usually, the DNA constructs will be suitable for replication in a unicellular host, such as yeast or bacteria, but may also be intended for introduction and integration within the gnome of cultured mammalian or other eukaryotic cell lines. DNA constructs prepared for introduction into bacteria or yeast will include a replication system recognized by the host, the N-myc DNA fragment encoding the desired polypeptide product, transcriptional and translational initiation regulatory sequences joined to the 5'-end of the N-myc DNA sequence, and transcriptional and translational termination regulatory sequences joined to the 3'-end of the N-myc sequence. The transcriptional regulatory sequences will include a heterologous promoter which is recognized by the host. Conveniently, available expression vectors which include the replication system and transcriptional and translational regulatory sequences together with an insertion site for the N-myc DNA sequence may be employed.

To be useful in the detection methods of the present invention, the polypeptides are obtained in substantially pure form, that is, typically about 50% w/w or more purity, substantially free of interfering proteins and contaminants. Preferably, the N-myc polypeptides are isolated or synthesized in a purity of at least about 80% w/w and, more preferably, in at least about 95% w/w purity. Using conventional protein purification techniques, homogeneous polypeptides of at least 99% w/w can be obtained. For example, the proteins may be purified by use of the antibodies described hereinafter using immunoadsorbent affinity chromatography. Such affinity chromatography is performed by first linking the antibodies to the solid support and then contacting the linked antibodies with the source of the N-myc proteins, e.g., lysates of cells which naturally produce N-myc or which produce N-myc as a result of introduction of a recombinant N-myc DNA molecule.

Once a sufficient quantity of N-myc polypeptide has been obtained, polyclonal antibodies specific for the N-myc protein may be produced by in vitro or in vivo techniques. In vitro techniques involve in vitro exposure of lymphocytes to the antigenic polypeptides, while in vivo techniques require the injection of the polypeptides into a wide variety of vertebrates. Suitable vertebrates are non-human, including mice, rats, rabbits, sheep, goats, and the like. Polypeptides having more than about 30 amino acids, particularly more than about 50 amino acids, may serve directly as immunogens. If the polypeptide is smaller than about 10 kD, particularly less than about 6 kD, it may be necessary to join the polypeptide to a larger molecule to elicit the desired immune response. The immunogens are then injected into the animal according to the predetermined schedule, and the animals are bled periodically with successive bleeds having improved titer and specificity. The injections may be made intramuscularly, intraperitoneally, subcutaneously, or the like, and usually an adjuvant, such as incomplete Freund's adjuvant, will be employed.

If desired, monoclonal antibodies can be obtained by preparing immortalized cell lines capable of producing antibodies having the desired specificity. Such immortalized cell lines may be produced in a variety of ways. Conveniently, a small vertebrate, such as a mouse, is hyperimmunized with the desired antigen by the method just described. The vertebrate is then killed, usually several days after the final immunization, the spleens removed, and the spleen cells immortalized. The manner of immortalization is not critical. Presently, the most common technique is fusion with a myeloma cell fusion partner, as first described by Kohler and Milstein (1976) Eur. J. Immunol. 6:511-519. Other techniques include EBV transformation, transformation with bare DNA, e.g., oncogenes, retroviruses, etc., or any other method which provides for stable maintenance of the cell line and production of monoclonal antibodies.

When employing fusion with a fusion partner, the manner of fusion is not critical and various techniques may be employed. Conveniently, the spleen cells and myeloma cells are combined in the presence of a nonionic detergent, usually polyethylene glycol, and other additives such as Dulbecco's Modified Eagle's Medium, for a few minutes. At the end of the fusion, the nonionic detergent is rapidly removed by washing the cells. The fused cells are promptly dispensed in small culture wells (usually in a microtiter plate) at relatively low density, ranging from about $1-5 \times 10^5$ per well, in a selective medium chosen to support growth of the hybrid cells while being lethal to the myeloma cells. Usually, the myeloma cell line has been mutated to be sensitive to a lethal agent, typically being HAT sensitive.

After sufficient time, usually from one to two weeks, colonies of hybrids are observed and plates containing hybrid positive wells are identified. The plates and wells having only one colony per well are selected, and supernatants from these wells are tested for binding activity against the N-myc protein or the isolated antigen. Once positive hybridomas are identified, the cell line can be maintained as viable cultures and/or by lyophilization and frozen storage.

Depending on the desired use for the antibodies, further screening of the hybridomas may be desirable. Hybridomas providing high titers are desirable. Furthermore, cytotoxic antibodies, e.g., IgG2a, IgG2b, IgG3 and IgM, may be selected for use in therapeutic treatment of colorectal cancers. For use in immunodiagnostic assays, antibodies having very high specificity for the antigenic site are desirable.

Once the desired hybridomas have been selected, monoclonal antibodies may be isolated from the supernatants of the growing colonies. The yield of antibodies obtained, however, is usually low. The yield may be enhanced by various techniques, such as injection of the hybridoma cell line into the peritoneal cavity of a vertebrate host which accept the cells. Monoclonal antibodies may then be harvested from the ascites fluid or the blood. Proteinaceous and other contaminants will usually be removed from the monoclonal antibodies prior to use by conventional technique, e.g., chromatography, gel filtration, precipitation, extraction, or the like.

By properly selecting polypeptides used as the immunogen, antibodies having high specificity and affinity for the N-myc protein can be obtained. The polypeptide selected should represent one or more epitopic sites which are unique to the N-myc protein and which can distinguish N-myc from closely related proteins such as c-myc. Such unique epitopes are found on polypeptides II and III shown above.

The polypeptides and antibodies of the present invention may be used with or without modification. Frequently, the polypeptides and antibodies will be labelled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescers, chemiluminescers, magnetic particles, and the like. Patents teaching the use of such labels include U.S. Pat.

Nos. 3,817,837; 3,850,752; 3,939,350; 3,996,345; 4,277,437; 4,275,149; and 4,366,241.

Antibodies and polypeptides prepared as described above can be used in various immunological techniques for detecting N-myc protein in biological specimens, particularly cell samples such as neurocytes, retina cells, and small lung cells (neuroendocrine-derived) and body fluid samples, including blood, plasma, serum, urine, and the like. Depending on the nature of the sample, both liquid phase assays and solid-phase immunohistochemical staining techniques will find use. Conveniently, immunohistochemical staining techniques may be used with cell samples including tissue samples, sputum, and lung lavage samples. For example, a tissue sample may be fixed in formalin, B-5, or other standard histological preservative, dehydrated and embedded in paraffin as is routine in any hospital pathology laboratory. Sections may then be cut from the paraffinized tissue block and mounted on glass slides. The N-myc protein, if present, may then be detected in the nucleus by exposure with labelled anti-N-myc antibody or exposure to unlabeled anti-N-myc antibody and a labelled secondary antibody. Sputum and lavage samples are typically prepared in a similar manner where the sample is first dehydrated by exposure to a dehydrating agent, typically a low molecular weight alcohol.

Liquid phase immunoassays or Western Blot analysis will also find use in the detection of the N-myc protein particularly in body fluids when the protein is shed into such fluids, e.g., blood or urine. Solid tissue and sputum samples may also be assayed in liquid phase systems by lysing the cellular sample in order to release the intracellular protein. Once the protein is released, the sample will be placed in a suitable buffer, the sample buffer subjected to a suitable immunoassay. Numerous competitive and non-competitive immunoassays are available and described in the scientific and patent literature.

The antibodies of the present invention may also find use in cancer therapy and other medical applications. For example, anti-N-myc antibodies, preferably human antibodies, may be coupled to toxins, such as diphtheria toxin and the ricin A chain, and administered to patients suffering from neural and neuroendocrine cancers. The use of antibody conjugated toxins in cancer therapy is described generally in U.S. Pat. Nos. 4,093,607; 4,340,535; 4,379,145; and 4,450,154. Antibodies aloe may also find use in treatment, particularly by blocking or interrupting the activity of the N-myc protein which contributes to the neoplastic phenotype.

The following experiments are offered by way of illustration and not by way of limitation.

EXPERIMENTAL

1 Preparation and Expression of Partial cDNA Clone of N-myc.

To characterize the N-myc gene and its gene product, a cDNA library was constructed from the LA-N-5 human neuroblastoma cell line using the Okayama-Berg vector (Okayama and Berg (1982) Mol. Cell Biol. 2:101). Approximately 80,000 clones were screened with pNb-1 which is a plasmid containing a human N-myc fragment isolated from a neuroblastoma cell line (Schwab et al. (1983), Supra.). One positive clone, designated N-myc 1, was obtained. Dideoxy sequencing of N-myc 1 was performed on independent M13 clones containing either overlapping fragments or complementary DNA strands. The nucleotide sequence together with the deduced amino acid sequence is shown in FIG. 1. The amino acids in FIG. 1 are numbered corresponding to the complete sequencing as reported by Kohl et al. (1986) Supra.

The largest open reading frame in N-myc 1 is 1182 nucleotides long and would encode the carboxyl terminal 394 amino acids of the putative N-myc protein. Comparison of the N-myc 1 sequence and that reported by Kohl et al. (1986) Supra. reveals only one notable difference between the large open reading frame from the N-myc 1 clone and the published sequence. The third base of the colon for amino acid 226 in the N-myc 1 clone is a cytosine, while the first base of the next colon is a guanine. The published sequence shows a reversal of these two residues. This difference results in a change in amino acid 227; i.e., alanine instead of proline.

A series of vectors for expressing portions of the putative N-myc encoded protein in *E. coli* were constructed by fusing the 5'-region of a bovine growth hormone gene (bGH) in frame, to six different regions of the N-myc 1 clone as follows:

| Fusion Gene | Amino Acid Nos.* | Symbol* |
| --- | --- | --- |
| bGH/N-myc I | 96–139 | ———— |
| bGH/N-myc II | 178–253 | - - - - - - |
| bGH/N-myc III | 178–277 | ·········· |
| bGH/N-myc IV | 256–310 | — ·· — |
| bGH/N-myc V | 311–409 | ∼∼∼∼ |
| bGH/N-myc VI | 410–464 | — — — |

*See FIG. 1.

The three sites in the bGH gene used for the fusion to N-myc specific sequences were SstI, PstI, and HindIII, generating fusion proteins containing 76, 92, and 114 residues of the amino terminus of bGH, respectively.

Expression vector p414/936, a modified temperature-sensitive runaway plasmid containing transcription termination and translation termination signals in all three reading frames adjacent to a polylinker used for introduction of genes linked to a tryptophan synthetase promoter (FIG. 2), was used for bGH/N-myc constructions I, III, IV, V and VI. The basic components of the p414/936 vector are: 1) a selectable drug marker, Amp ®; 2) transcription termination signal, and 3) a poly linker containing translation termination signals in all three reading frames shown in boxes. All five fusion genes expressed using this vector were promoted by a tryptophan synthetase promoter depicted by the black box. The bGH/N-myc genes, including the promoter, were all cloned into the EcoRI site 5' to the promoter and at either the HpaI, BamHI or SstII sites (underlined) at the 3'-end of the genes. The specific 3'-cloning site is shown in brackets beside each construct. The shaded portion of each bar construct represents the bGH domain, while the open portion represents the N-myc domain. The number of amino acids representing either bGH or N-myc in each construct is shown in brackets within each bar construct. In addition, the letters opposite the bracketed numbers in the shaded portion refer to the restriction endonuclease sites in bGH where the N-myc gene segments were fused: H (HindIII), S (SstI), and P (PstI). bGH/N-myc I was constructed by cloning the MluI/BamHI fragment (FIG. 1) of N-myc into M13mp20. The N-myc fragment was then recovered by cleavage with HindIII and SstII for cloning into the p414/936 expression vector with the appropriate bGH fragment (EcoRI/HindIII). bGH/N-myc III was generated by cleaving N-myc 1 with TaqI and blunt ending the site by filling in the appropriate nucleotides with Klenow. N-myc 1 was then cut with SstI and the N-myc fragment ligated to the vector as shown above. bGH/N-myc IV was constructed by cloning the small N-myc MspI fragment into M13mp10 (AccI) and recovering it by cleavage with PstI and BamHI. bGH/N-myc V was formed in the same manner as bGH/N-myc IV, using the largest MspI fragment of N-myc 1. Finally, bGH/N-myc VI was generated using an MspI/HindII fragment of N-myc 1 cloned into M13mp8 (AccI/HindII). The fragment was recovered using HindIII and HindII for cloning into the vector. The dotted portion of the bar construction for bGH/N-myc VI represents the 3'-untranslated sequence present in this construction.

Fusion gene bGH/N-myc II was expressed using vector pCFM414 previously described for obtaining expression of the human c-myb antigen. bGH/N-myc II was constructed by ligating an SstI/RsaI fragment of N-myc 1 in frame with the SstI site in the bGH gene and allowing the encoded product to terminate at a stop codon provided in the vector.

The above-described vectors were then expressed in E. coli as follows.

2. Preparation of Antisera in Rabbits

The bGH/N-myc fusion proteins obtained as described above were used to produce polyclonal antisera in rabbits by the method described by Slamon et al. (1985) Science 228:1427.

3. Characterization of the N-myc Protein Using the Polyclonal Antisera

Antisera generated to the various N-myc protein fragments were tested in a liquid phase immunoprecipitation assay using human neuroblastoma cell lines (LA-N-5 and IMR-32) known to express N-myc transcripts, but not c-myc. The human promyelocytic cell line, HL-60, was used as a negative control, since these cells express high levels of c-myc transcripts, but not N-myc. In addition, two other human cell lines, the HT 29 (colon carcinoma) and U251 (glioma), were used as negative controls since neither express N-myc transcripts. The criteria used to identify a protein as N-myc encoded were two-fold. First, the protein had to be immunoprecipitated from neuroblastoma cell lysates by antisera to at least two different N-myc-encoded fragments representing separate areas of the putative amino acid sequence, thus greatly reducing the possibility that the immunoprecipitation was due to chance sequence homology between the vector-expressed fragment and a cellular protein other than N-myc. Second, the protein should not be found in other human tumor cell lines (including the neural derived glioma cells) where the N-myc transcript is not found.

Using these criteria, a protein appearing as a doublet of 62 kD and 64 kD was consistently immunoprecipitated from LA-N-5 human neuroblastoma cells by antibody directed to each of the six N-myc fragments generated in E. coli. Similar results were seen for the IMR-32 human neuroblastoma cell line. Immunoprecipitation of this protein could be completely removed in all cases by competition with the appropriate N-myc fragment, indicating a specific antigen antibody reaction. Moreover, immunoprecipitation of the 62–64 kD doublet could not be blocked when non-homologous antibody and antigen combinations were used; i.e., attempts to block precipitation mediated by antisera to fragment II with fragment I antigen were unsuccessful, again indicating that the precipitation is due to a specific antigen-antibody reaction. Finally, to ensure that the precipitation of the 62–64 kD protein was due to antibodies directed to the N-myc and not the bGH portion of the fusion protein, bGH alone was added to the reaction mix. In no instance did the bGH inhibit the precipitation of the 62–64 kD protein.

The c-myc protein is similar in size (64–67 kD) and appearance (doublet) to the N-myc protein (Hann and Eisenman (1984) Mol. Cell Biol. 4:2486). Evidence that this is not the c-myc protein, however, is provided by two sets of data. First, the protein identified using the anti-bGH/N-myc fusion antibodies is found in cells (LA-N-5) which lack detectable c-myc transcripts. Second, five of the six antisera fail to identify any specific protein when used in immunoprecipitation assay with lysate from the HL-60 cell line which is rich in c-myc transcripts, indicating that they do not recognize the c-myc protein. The antisera directed against N-myc fragment V did recognize a 64–67 kD doublet in lysate from HL-60 cells on long exposure (96 hours) of the immunoprecipitation radioautograph. Comparison of the deduced amino acid sequence from this fragment of N-myc and the analogous area in the c-myc protein shows significant sequence homology which would account for the ability of this antiserum to recognize the c-myc protein. None of the anti-bGH/N-myc antisera precipitated a 62–64 kD protein in the U251 or HT-29 control cell lines. Thus, the data demonstrate that the 62–64 kD protein is the N-myc-encoded protein.

Several aspects of the biochemistry and biology of the N-myc protein were investigated using the N-myc-specific antisera. To determine if the N-myc protein was phosphorylated, LA-N-5 cells were metabolically labelled in phosphate-free media with $^{32}P$-orthophosphate (ICN Biochemicals, Inc., Irvine, Calif.) by the method of Osterman, in: Methods of Protein and Nucleic Acids Research, Springer-Verlag, New York, N.Y., 1984, pp. 144–150. The lysate was then subjected to immunoprecipitation using antisera to the bGH/N-myc II fusion protein and analyzed on SDS-PAGE gel. A band at 62–64 kD was found to be labelled with $^{32}P$-orthophosphate. Thus, like c-myc, the N-myc protein is a phosphoprotein.

The level of N-myc protein synthesis in LA-N-5 neuroblastoma cells compared to other cellular proteins was estimated using an immunoprecipitation assay. In these experiments, a known amount of radioisotope-labelled whole cell lysate was subjected to immunoprecipitation using a combination of N-myc-specific antisera (anti-bGH/N-myc II and IV). The resulting precipitated proteins were then subjected to SDS-PAGE (sodium dodecyl sulfate-polyacrylamide gel) analysis, and the doublet band at 62–64 kD was eluted from the gel, counted and compared to the total trichloroacetic acid-preciptable counts in the whole cell lysate as described by Slamon et al. (1985), supra. Approximately 0.076% of the total $^{35}S$-methionine incorporation in these cells was associated with the 62–64 kD N-myc protein.

The kinetics of intracellular turnover of the N-myc protein were determined by pulse-chase labelling experiments. LA-N-5 human neuroblastoma cells were labelled with $^{35}$S-methionine for sixty minutes and chased with excess unlabeled methionine (Slamon et al. (1985), supra.). The half-life of the p62-64$^{N\text{-}myc}$ doublet was between 30-50 minutes. Again, this feature of the N-myc protein is shared with c-myc, which has a half-life of 20-30 minutes.

To determine the subcellular localization of the N-myc protein, each of anti-N-myc antisera were used in immunocytochemical analyses of LA-N-5 cells. Using an indirect immunoperoxidase staining procedure and dilutions of N-myc antisera of 1:2000 to 1:4000 by volume, a strong staining reaction was noted in the nuclei of the cells. All cells showed nuclear staining; however, variable intensity of the stain from cell to cell, indicating heterogeneity in N-myc protein content. While all six of the anti-N-myc antisera recognized the 62-64 kD protein in LA-N-5 cells by immunoprecipitation assay, under the conditions tested only three of these sera stained the neuroblastoma cells histochemically, anti-N-myc II, III and V. The fact that anti-N-myc sera I, IV and VI did not react immunocytochemically could be due to fixative-mediated alterations of the antigenic determinants to which the non-reacting antisera are directed. Conversely, these regions of the protein may be unavailable for recognition by the particular antisera, due to interactions of the antigenic regions with other cellular macromolecules or to the tertiary structure of N-myc within intact cells. To determine the specificity of the cytochemical reaction, HL-60 cells were used as a control cell line. Two of the three antisera (bGH N-myc II and III) did not stain HL-60 cells, indicating specificity for the N-myc protein. The antisera directed against N-myc fragment V stained both LA-N-5 and HL-60 cells. As with the immunoprecipitation data, the ability of this antiserum to immunocytochemically recognize both the N-myc and c-myc proteins is likely due to the high degree of homology between the two proteins in this region.

The nuclear localization of the 62-64 kD protein was confirmed by biochemical fractionation of LA-N-5 cells into nuclear, cytoplasmic and membrane fractions as described by Slamon et al. (1985) supra. The data placed the majority of the N-myc protein within the nucleus of neuroblastoma cells, and thus were consistent with those obtained by immunocytochemical analysis. Experiments to evaluate the subnuclear localization of the N-myc protein were done by obtaining intact nuclei from LA-N-5 cells and subjecting them to differential fractionation. The nuclei were fractionated into three components; nucleoplasm, chromatin and nuclear matrix as described by Boyle et al. (1985) Mol. Cell Biol. 5:3017. These fractions were then separately tested in immunoprecipitation assays using the N-myc specific anti-N-myc II antiserum. The majority of the N-myc protein was found associated with the nuclear matrix.

Again, this is a feature which N-myc shares in common with c-myc.

Finally, to demonstrate the clinical diagnostic potential of the N-myc antisera, sections of primary human neuroblastoma tumors were tested using immunohistochemical techniques. In these experiments, only N-myc-specific antisera were used; i.e., anti-N-myc fragment II. As with cultured cell staining, the antiserum was used at dilutions of 1:2000 to 1:4000. Tissue from two separate primary tumors were examined; one from a patient with stage II disease, and one with stage IV disease. In both instances, there was intense and specific staining of malignant neuroblasts, with virtually no staining of the adjacent vascular or stromal tissue. The tumor from the patient with stage II disease was stroma rich, with nodular areas of undifferentiated cells. This tumor was shown to contain one copy of the N-myc oncogene by Southern Blot analysis (Seeger et al. (1985), Supra. The tumor from the patient with stage IV disease consisted of predominantly undifferentiated neuroblasts with surrounding vascular and stromal elements. It was shown to contain 200 copies of the N-myc oncogene (Id.)

Although the foregoing invention has been described in some detail by way of illustration and example for purposes of clarity of understanding, it will be obvious that certain changes and modifications may be practiced within the scope of the appended claims.

What is claimed is:

1. A polypeptide, consisting of an amino acid sequence selected from the group consisting of

| | | | |
|---|---|---|---|
| (I) | AFGLGGLGGL LERAVSEKLQ | TPNPVILQDC HGRG; | MWSGFSAREK |
| (II) | ELAHPAAECV APASAPAAGP RPGGRQTSGG | DPAVVFPFPV AVASGAGIAA DHKALS; | NKREPAPVPA PAGAPGVAPP |
| (III) | ELAHPAAECV APASAPAAGP RPGGRQTSGG DEEEDEEEEI; | DPAVVFPFPV AVASGAGIAA DHKALSTSGE | NKREPAPVPA PAGAPGVAPP DTLSDSDDED |
| (IV) | GEDTLSDSDD RSSSNTKAVT | EDDEEEDEEE TFTITVRPKN | EIDVVTVEKR AALGP; and |
| (V) | ELVKNEKAAK LLLEKEKLQA | VVILKKATEY RQQQLLKKIE | VHSLQAEEHQ HARTC. |

2. A polypeptide as in claim 1, wherein the amino acid sequence is selected from the group consisting of (II) and (III).

3. An antigenic or haptenic polypeptide defining an epitopic site which is immunologically cross-reactive with both N-myc and c-myc protein wherein the polypeptide consists of the following amino acid sequence:

| | | |
|---|---|---|
| GRAQSSELIL SEDAPPQKKI SPRNSDSEDS FLTLRDHVP | KRCLPIHQQH KSEASPRPLK ERRRNHNILE | NYAAPSPYVE SVIPPKAKSL RQRRNDLRSS |

* * * * *